United States Patent
Board et al.

(10) Patent No.: US 6,499,350 B1
(45) Date of Patent: Dec. 31, 2002

(54) TURBINE ENGINE FOREIGN OBJECT DAMAGE DETECTION SYSTEM

(75) Inventors: David B. Board, Boca Raton, FL (US); Craig E. Hughes, Oviedo, FL (US)

(73) Assignee: Swantech, L.L.C., Fort Lauderdale, FL (US)

( * ) Notice: Subject to any disclaimer, the term of this patent is extended or adjusted under 35 U.S.C. 154(b) by 0 days.

(21) Appl. No.: 09/542,099

(22) Filed: Apr. 4, 2000

(51) Int. Cl.[7] .............................................. G01N 29/00
(52) U.S. Cl. ............................ 73/660; 73/593; 73/602; 73/770
(58) Field of Search ...................... 73/660, 662, 760, 73/767, 770, 593, 801; 324/618, 537; 340/269

(56) References Cited

U.S. PATENT DOCUMENTS

| | | | |
|---|---|---|---|
| 3,798,626 A | * 3/1974 | Weichbrodt et al. | 73/660 |
| 4,530,240 A | * 7/1985 | Board et al. | 73/593 |
| 4,887,468 A | * 12/1989 | McKendree et al. | 73/660 |
| 4,896,537 A | * 1/1990 | Osborne | 73/660 |
| 5,101,162 A | * 3/1992 | Webster et al. | 324/618 |

* cited by examiner

Primary Examiner—Hezron Williams
Assistant Examiner—Jacques M. Saint-Surin
(74) Attorney, Agent, or Firm—Malin, Haley & DiMaggio, P.A.

(57) ABSTRACT

A Foreign Object Damage (FOD) detection system is disclosed for detecting and analyzing ultrasound or stress waves emitted when an object enters the intake of a turbine engine and impacts one or more of the blades in the engine. Upon detection the FOD detection system can immediately inform the operator, inform another electronic device (computer, etc.) and/or latch the event for review by maintenance personnel. The detection system generally consists of one or more stress wave sensors and an electronic assembly to process the stress wave signal received from the sensor(s). The electronic assembly is in communication with the sensor(s) via conventional cabling.

20 Claims, 2 Drawing Sheets

TURBINE ENGINE FOREIGN OBJECT DAMAGE DETECTION SYSTEM

BACKGROUND OF THE INVENTION

1. Field of the Invention

The present invention is generally directed to stress wave analysis and particularly to the use and analysis of stress waves to detect foreign object damage (FOD) in turbine engines; such as, but not limited to, jet aircraft.

2. Description of Related Art

Foreign object damage ("FOD") has always been a major concern of turbine engine manufacturers and users. Damaged fan, compressor and turbine blades in an engine can result in catastrophic failure or a loss of operating efficiency. To prevent FOD, some turbine systems use filters. However, this is not practical in all cases, due to size, weight, and performance issues created by filters. In non-filtered systems, periodic manual inspection is used to detect any damage at an unknown time after-the FOD event. This unknown leaves a window for the damage to propagate into a catastrophic failure that would endanger lives and/or equipment. Also, manually inspecting all, the blades is a time consuming and costly process. Accordingly, what is needed in the art is a system for detecting foreign object damage to equipment, such as turbine engines, which detects the damage in a timely and cost effective manner. It is therefore to the effective resolution of the shortcomings of the prior art that the present invention is directed.

BRIEF SUMMARY OF THE INVENTION

The present invention provides a FOD detection system consisting of at least one and preferably a plurality of stress wave sensors mounted on an engine at locations that provide transmission path from the fan bearing housing(s), a cable to interface the sensor(s) with the electronics, and an electronic assembly. The electronic assembly conditions the received signal, demodulates the sigrialds and processes the signal to determine/notify if a FOD event occurred. The sensors are preferably externally mounted to the engine. Thus, by using multiple sensors located along the length of the engine, the system can detect the depth that an object has traveled into the engine before the object was destroyed Accordingly, the present invention provides for the detection of a slow energy event in an extremely high energy environment, without the need of a highly trained professional to analyze data, and also gives a real time indication that a FOD event has occurred. The use of the present invention with a turbine engine should increase the safety efficiency and reliability of such engine.

Accordingly, it is an object of the present invention to provide a system for detecting and analyzing foreign object damage to a piece of equipment or machinery such as a turbine engine.

It is another object of the present invention to provide a system for detecting and analyzing foreign object damage in a relatively timely and cost efficient manner.

It is still another object of the invention to use stress wave signals to detect foreign object damage in a turbine engine.

It is even still another object of the present invention to reduce damage to turbine engines from ingestion of foreign object(s).

It is yet another object of the present invention to improve the reliability of turbine engines.

In accordance with these and other objects which will become apparent hereinafter, the instant invention will now be described with particular reference to the accompanying drawings.

DETAILED DESCRIPTION OF THE INVENTION

Figure 1:
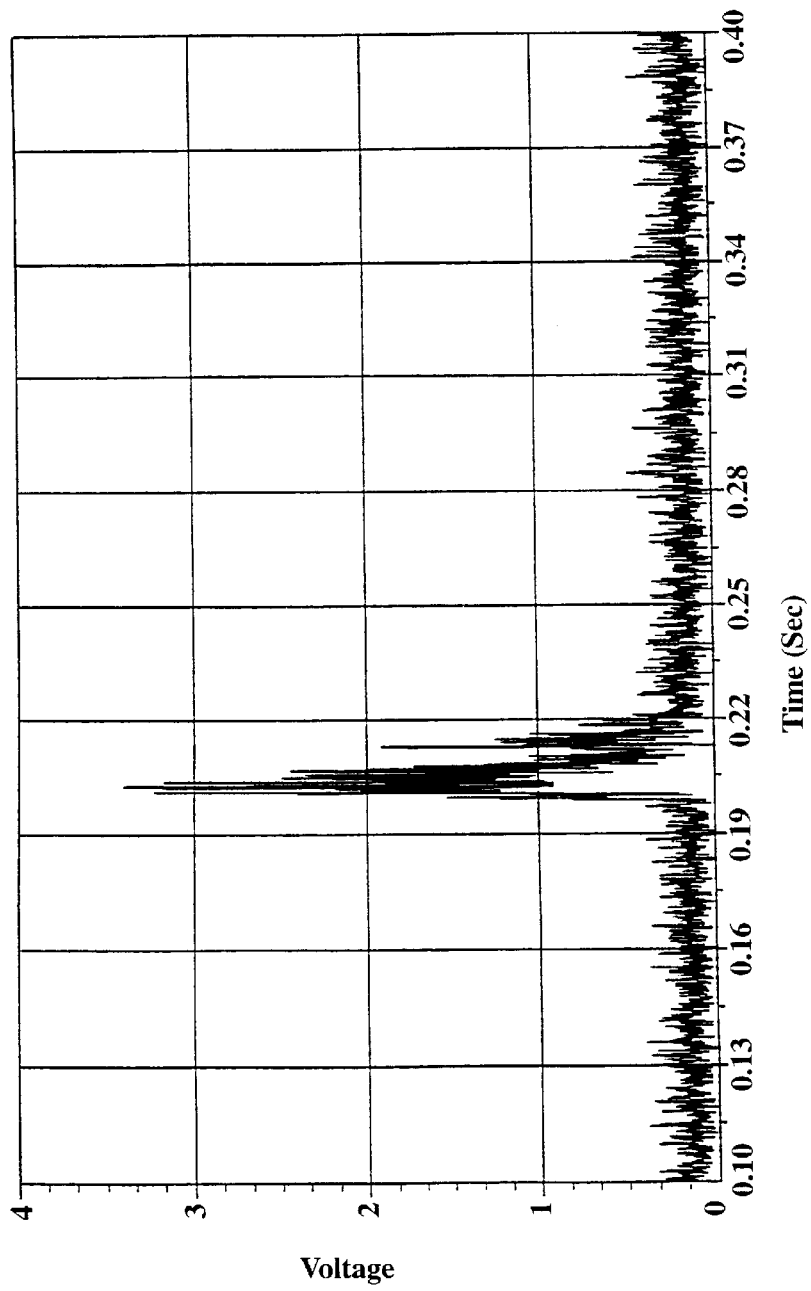
FIG. 1 is a graph illustrating the increase in stress waves to detect foreign object damage at impact.

The present invention generally consists of one or more stress wave sensors 20 and an electronic assembly to process the stress wave signal received from sensor(s) 20. The electronic assembly is in communication with sensors 20 via conventional cabling. In one embodiment, sensor 20 can include amplification and band pass filtering of the stress wave signal at the sensing element. Alternatively, a non-amplified sensor 20 can also be used, preferably with the use of greater stress wave signal amplification outside the sensing element and a lower noise floor than the preferred amplifying and filtering sensor.

Preferably, the stress wave frequency of interest ranges from 20 KHz up. However, other values and ranges can be used and/or analyzed and all are considered within the scope of the invention. To reduce the stress wave signal amplitude range and the signal conditioning electronics' sensitivity sensor 20 may incorporate two features: gain and band pass filtering. In one embodiment, the preferred frequency of interest can be 38 KHz, sensor 20 can have a gain of 72 dB referenced at preferably 100 Hz and band pass filtration can be centered at 38 KHz. Again these values are provided by way of example and are not considered limiting, and other values can be used and are considered within the scope of the invention.

Even with the amplification at sensor 20, the stress wave signal may need additional amplification. This determination is typically a function of the type and power output of the engine being tested. Therefore, an amplifier may be needed in the electronic assembly. The FOD detection system design 10 also preferably includes band pass filtering. Because an impact event resembles an impulse function, a broad frequency band of signals are created by the event. At low frequencies these signals are typically a very low percentage of the overall signal, and would require extreme sensitivity to detect. But at the higher frequencies (i.e. above 20 KHz) the impact signal typically rises out of the background noise by a factor of two or more. This high frequency characteristic is important in selecting the frequency of interest, such as the 38 KHz frequency discussed above by way of example. To further separate the frequency of interest from the background signal, a band pass filter 30 designed around the frequency of interest can be used. The bandwidth can vary depending on the sensor and type of engine. In one embodiment, the filter can be designed to have a 7 KHz pass band.

Depending on the stress wave signal strength, an amplifier may be needed in between band pass filter 30 and the demodulator to insure optimum performance.

An. amplitude demodulator performs the final stage of the signal conditioning. The resulting signal can be referred to as the stress wave pulse train ("SWPT"), and the area under the resulting curve can be referred to as the stress wave energy ("SWE").

At this point the SWPT must be processed by either analog or digital means to detect the pulse created by the FOD impact event. Detecting the pulse is used for identifying a FOD event. There are many conventional methods that could be used to detect a pulse, which would be obvious to one having ordinary skill in the art. The present invention uses a threshold, preferably provided as software, or alternatively as analog hardware, which is based on (1) the average SWPT, (2) an integrator to determine the SWE above the threshold, and (3) a SWE threshold to eliminate spurious noise from the input signal. The preferred pulse detecting method using a threshold results in a robust peak detection method that allows ample adjustment for various types of engines. The mathematical definition and equation (preferably incorporated into pulse detecting software or alternatively into analog hardware) is the following:

$$T_{peak} = \overline{SWPT} * T_{set}$$

$$D_{peak} \begin{cases} 1, & \text{if } SWPT \geq T_{peak} \\ 0, & \text{if } SWPT < T_{peak} \end{cases}$$

$$SWE_{peak} = D_{peak} * \int (SWPT - T_{peak})$$

$$\text{Fault} = \begin{cases} 1, & \text{if } SWE_{peak} \geq Fault\tilde{G}\{|H \\ \Sigma^0, & \text{if } SWE_{peak} < \text{Fault} \end{cases}$$

Where: $T_{set}$=Threshold set point referenced to average SWPT.

$T_{peak}$=Threshold Voltage.

$D_{peak}=T_{peak}$ exceeded equals 1 otherwise 0.

$SWE_{peak}$=peak energy above $T_{peak}$

Figure 2:
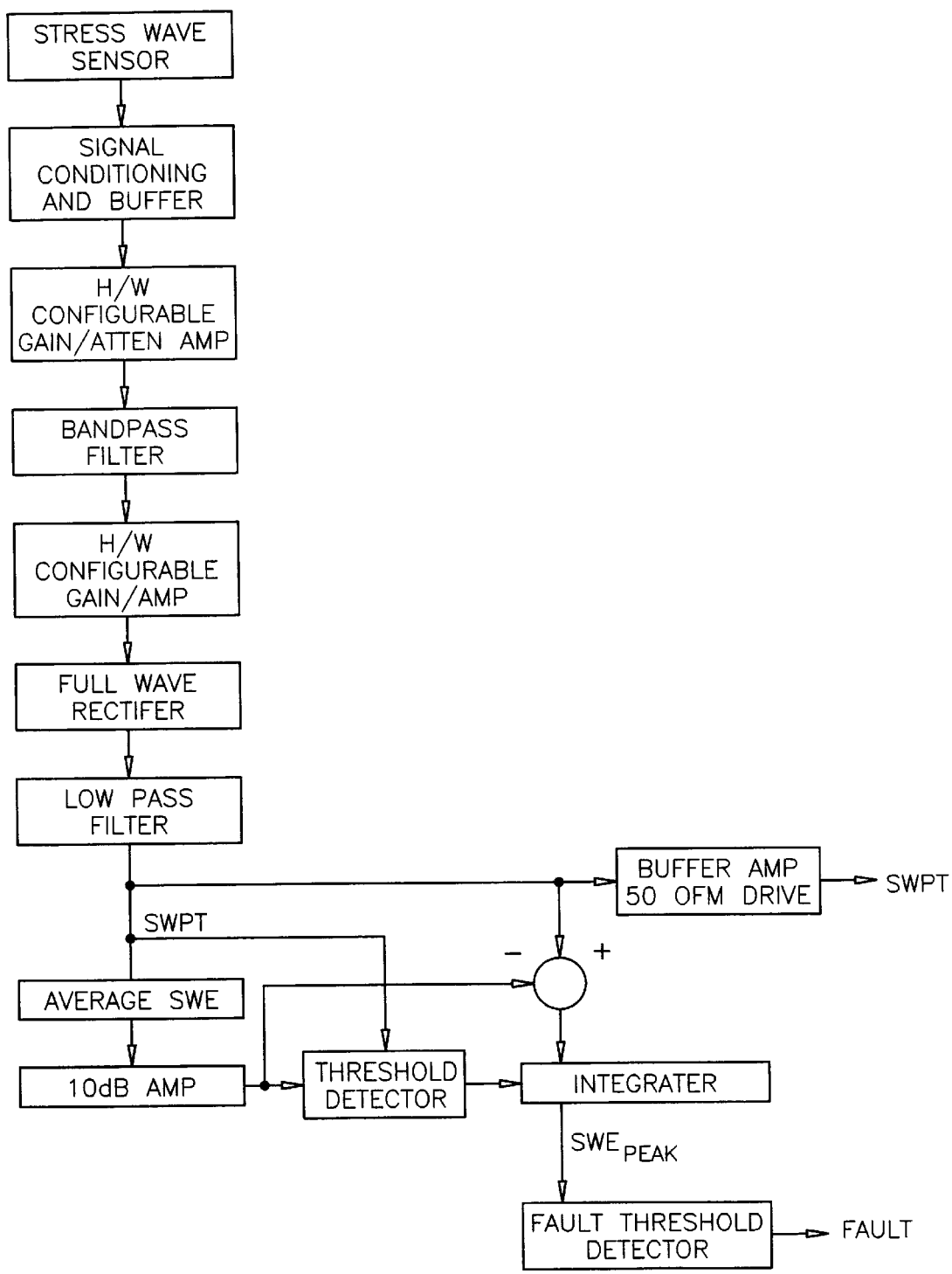
FIG. 2 is a block diagram for the foreign object damage detection and analysis system of the present invention.

The output of the SWE threshold detector is binary and represents a pass or a fail condition. The output signal can be used to trip a variety of indicators, to issue a warning to the air crew, ground crew or other individuals, that a FOD event has been detected. In one embodiment, the present invention uses a latching indicator, however, the output could be monitored real time to detect the transition(s). One embodiment 10 for the present invention FOD Detection System Block Diagram is illustrated in FIG. 2.

The detection and analysis of stress waves can be used to identify that a FOD event has occurred and how deep into the engine the FOD progressed. In the case of aircraft turbine engines this would drastically reduce the risk of engine failure due to a progressive failure initiated by a FOD event. With the use of stress waves, the present invention allows for detection of FOD at impact, not hours, days, weeks or months later (see FIG. 1).

The present invention has also shown that materials that are considered non-damaging, do not create a signal that would give false alarms. This is due to the fact that the amplitude of the stress waves is proportional to the energy transferred to the fan/turbine blade at impact. This stress wave signal can then be processed through analog or digital means to detect the FOD event.

Certain aspects of the present invention include the following: (a) stress waves can be used to detect FOD events in a turbine engine; (b) peak detection methods (digital or analog) can be used to monitor conditioned stress wave signals to detect the FOD event; (c) an integrator (digital or analog) can be used to determine the stress wave energy, followed by a threshold detector to minimize false alarms; (d) a stress wave signal can be averaged then amplified to set a peak detection threshold, via digital or analog means; and (e) a stress wave signal can be amplified, and band pass or high pass filtered to minimize background signals.

The present invention is suitable for use in many applications that require the detection of an impact event within operating machinery, and all of such applications are considered within the scope of the invention. Accordingly, the invention is not limited to its above-described use for detection of FOD events within turbine engines, in particular aircraft jet engines.

In lieu of conventional cabling, the sensors can communicate with the electronics of the system through wireless technology.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method for detecting foreign object damage in a piece of machinery, said method comprising the following steps:

(a) receiving a stress wave signal produced by the piece of machinery from a stress wave sensor;

(b) filtering of the received stress wave signal to eliminate frequencies at least below 20 kHz;

(c) demodulating the filtered stress wave signal to yield a stress wave pulse train;

(d) analyzing said stress wave pulse train to determine if a machinery damage threshold has been exceeded; and (e) generating an indicator when said machinery damage threshold has been exceeded;

wherein step (d) includes dynamically averaging the stress wave pulse train to set a dynamically adjustable peak threshold voltage.

2. The method for detecting foreign object damage of claim 1 wherein said threshold corresponds to a degree of damage to the piece of machinery.

3. The method for detecting foreign object damage of claim 1 further including the step of amplifying said received stress wave signal.

4. The method for detecting foreign object damage of claim 1 wherein step (d) includes the step of providing an integrator to determine a stress wave energy value and step (e) includes the step of using a threshold detector to minimize false alarms.

5. The method for detecting foreign object damage of claim 1 wherein said filtering step consist of band pass filtering of the stress wave signal around a frequency of interest of approximately 38 kHz.

6. The method for detecting foreign object damage of claim 5 wherein the band pass filtering has an approximate 7 kHz pass band.

7. A method for detecting foreign object damage in a piece of machinery, said method comprising the following steps:

(a) receiving a stress wave signal produced by the piece of machinery;

(b) analyzing said stress wave signal to determine if the signal exceeds a threshold; and (c) generating an indicator when said stress wave signal exceeds said threshold;

wherein step (b) includes the step of demodulating the received stress wave signal into a stress wave pulse;

wherein said threshold is determined by the following peak detection equation:

$$T_{peak} = \overline{SWPT} * T_{set}$$

$$D_{peak} = \begin{cases} 1, & \text{if } SWPT \geq T_{peak} \\ 0, & \text{if } SWPT < T_{peak} \end{cases}$$

$$SWE_{peak} = D_{peak} * \int (SWPT - T_{peak})$$

$$Fault \begin{cases} 1, & \text{if } SWE_{peak} \geq Fault \\ 0, & \text{if } SWE_{peak} < Fault \end{cases}$$

Where $T_{set}$=Threshold set point referenced to average SWPT.

$T_{peak}$=Threshold Voltage.

$D_{peak}$=$T_{peak}$ exceeded equals 1 otherwise 0.

$SWE_{peak}$=peak energy above $T_{peak}$.

8. A system for detecting foreign object damage to a piece of machinery, said system comprising:
    at least one stress wave sensor associated with the piece of machinery;
    an electronic assembly in communication with said at least one sensor; said electronic assembly providing band pass filtering of a stress wave signal received from said at least one stress wave sensor and demodulating the band pass filtered stress wave signal to yield stress wave pulses, said electronic assembly analyzes the stress wave pulses to determine if damage has been caused to the piece of machinery from an unintended ingested foreign object;
    wherein said electronic assembly including means for dynamically averaging the stress wave pulses to set a dynamically adjustable peak threshold voltage.

9. The system of claim 8 wherein said stress wave sensor detects stress wave signals of 20 KHz or higher.

10. The system of claim 8 wherein said electronic assembly communicates with said at least one sensor through cabling.

11. The system of claim 8 wherein said piece of machinery is a turbine engine.

12. The system of claim 8 wherein said electronic assembly is analog based.

13. The system of claim 8 wherein said electronic assembly is digital based.

14. The system of claim 8 wherein said electronic assembly includes means for amplifying the stress wave signals received from said sensor.

15. The system of claim 8 wherein said at least one sensor is a plurality of stress wave sensors positioned at various points along the piece of machinery.

16. The system of claim 8 wherein said electronic assembly detecting the stress wave pulses that exceed a predetermined threshold level.

17. The system of claim 8 wherein said electronic assembly communicates with said at least one sensor through wireless technology.

18. A method for detecting object damage in a piece of machinery, said method comprising the following steps:
    (a) conditioning a stress wave signal received by a stress wave sensor produced by the piece of machinery;
    (b) band pass filtering of the received stress wave signal;
    (c) demodulating the band pass filtered stress wave signal to yield a stress wave pulse train; and
    (d) processing the stress wave pulse train to determine if an unintended object damage event has occurred to the piece of machinery;
    wherein step (d) includes dynamically averaging the stress wave pulse train to set a dynamically adjustable peak threshold voltage.

19. The method for detecting foreign object damage of claim 18 wherein a frequency of interest for the band pass filtering is approximately 38 kHz and the band pass filtering has an approximate 7 kKz pass band.

20. A method for detecting object damage in a piece of machinery, said method comprising the following steps:
    (a) receiving a stress wave signal produced by the piece of machinery; and
    (b) analyzing said stress wave signal to determine if the signal exceeds a threshold;
    wherein said threshold is determined by the following peak detection equation:

$$D_{peak} = \begin{cases} 1, & \text{if } SWPT \geq T_{peak} \\ 0, & \text{if } SWPT < T_{peak} \end{cases}$$

$$SWE_{peak} = D_{peak} * \int (SWPT - T_{peak})$$

$$Fault \begin{cases} 1, & \text{if } SWE_{peak} \geq Fault \\ 0, & \text{if } SWE_{peak} < Fault \end{cases}$$

Where $T_{set}$=Threshold set point referenced to average SWPT.

$T_{peak}$=Threshold Voltage.

$D_{peak}T_{peak}$ exceeded equals 1 otherwise 0.

$SWE_{peak}$=peak energy above $T_{peak}$.

* * * * *